(12) United States Patent
Rashtchian et al.

(10) Patent No.: US 7,470,515 B2
(45) Date of Patent: Dec. 30, 2008

(54) COMPOSITIONS AND METHODS FOR CDNA SYNTHESIS

(75) Inventors: Ayoub Rashtchian, Gaithersburg, MD (US); David M. Schuster, Poolesville, MD (US)

(73) Assignee: Quanta Biosciences, Gaithersburg, MD (US)

( * ) Notice: Subject to any disclaimer, the term of this patent is extended or adjusted under 35 U.S.C. 154(b) by 0 days.

(21) Appl. No.: 11/237,922

(22) Filed: Sep. 29, 2005

(65) Prior Publication Data

US 2006/0068436 A1 Mar. 30, 2006

Related U.S. Application Data

(62) Division of application No. 10/653,416, filed on Sep. 3, 2003.

(60) Provisional application No. 60/407,248, filed on Sep. 3, 2002.

(51) Int. Cl.
*C12Q 1/68* (2006.01)
*C12P 19/34* (2006.01)
*C07H 21/04* (2006.01)

(52) U.S. Cl. .................. 435/6; 435/91.21; 536/24.33

(58) Field of Classification Search .............. 435/6, 435/91.21; 536/24.33, 22.1
See application file for complete search history.

(56) References Cited

U.S. PATENT DOCUMENTS

| | | | |
|---|---|---|---|
| 5,561,058 A | 10/1996 | Gelfand et al. | |
| 5,614,387 A | 3/1997 | Shen et al. | |
| 5,693,517 A | 12/1997 | Gelfand et al. | |
| 5,919,900 A | 7/1999 | Moyle et al. | |
| 6,087,489 A | 7/2000 | Dean | |
| 6,214,542 B1 | 4/2001 | Striker et al. | |
| 6,300,069 B1 * | 10/2001 | Missel et al. | 435/6 |
| 6,300,073 B1 | 10/2001 | Zhao et al. | |
| 6,406,891 B1 * | 6/2002 | Legerski | 435/91.1 |
| 6,416,989 B1 | 7/2002 | Abad et al. | |
| 6,495,350 B1 | 12/2002 | Lee et al. | |
| 6,521,411 B2 | 2/2003 | Hecker et al. | |
| 6,767,724 B2 | 7/2004 | Lee et al. | |

FOREIGN PATENT DOCUMENTS

| | | |
|---|---|---|
| WO | 01/00820 | 1/2001 |
| WO | WO 01/00820 A2 * | 1/2001 |

OTHER PUBLICATIONS

Peng et al. Multiple PCR analyses on trace amounts of DNA extracted from fresh and paraffin wax embedded tissues after random hexamer primer PCR amplification. J Clin Pathol., vol. 47, p. 605-608, 1994.*
Boehringer Mannheim 1997 Biochemicals Catalog, pp. 146-147, 150-153, and an instruction Manual from Tital RT-PCR system, Cat. No. 1855476.
"*Protocols and Applications Guide, Third Edition*", Promega Protocols and Applications Guide, 1996, pp. 181-189.
"*Stratagene Catalog: RT-PCR Systems and Kits*", Stratagene Calalogue, 1999, pp. 154-155, XP002264374.

* cited by examiner

*Primary Examiner*—Suryaprabha Chunduru
(74) *Attorney, Agent, or Firm*—Proskauer Rose LLP

(57) ABSTRACT

Methods for making cDNA molecules, for amplification of RNA by PCR and for preparation of cDNA libraries are provided. Kits for making cDNA molecules also are provided. Compositions are also provided comprising mixtures of reagents, including reverse transcriptases, buffers, cofactors and other components, suitable for immediate use in conversion of RNA into cDNA and RT PCR without dilution or addition of further components. These compositions are useful, alone or in the form of kits, for cDNA synthesis or nucleic acid amplification (e.g., by the Polymerase Chain Reaction) or for any procedure utilizing reverse transcriptases in a variety of research, medical, diagnostic, forensic and agricultural applications.

20 Claims, No Drawings

```
                        SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
cagcggccag acagttcctg                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 2
tgcccaccgt cgttctcgt                                               19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
cccaactcca gtgaataaca                                              20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 4
agaatggcgc ttaggactt                                               19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
actgcggtca aaaatgtccc                                              20
```

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
tctccagaac ggcttgatac ag                                     22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gcaggaccag ggcgttatag                                        20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
cgtcatggca agtgtgtcaa a                                      21

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
cagtcttggc acccacat                                          18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
agctctgctg gagaacctaa                                        20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
aatccgcggc aggggtatt                                         19

<210> SEQ ID NO 12
<211> LENGTH: 19
<212> TYPE: DNA
<213> ORGANISM: Artificial Sequence
<220> FEATURE:

<223> OTHER INFORMATION: Description of Artificial Sequence: Primer

<400> SEQUENCE: 12
tgggagctgc cccttgaga                                                   19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13
gaaggtgaag gtcggagtc                                                   19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
gaagatggtg atgggatttc                                                  20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
ggctacagct tcaccaccac                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
tggccatctc ttgctcgaag                                                  20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
ccggtggacc acgaagagt                                                   19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18
gctcgcctct tccatgtctc                                                  20

```
<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 19
cggtcaggca cacaaggg                                                 18

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 20
gcatacacac aacaaaatgg ca                                            22

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 21
cggcggcggg cagtt                                                    15

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 22
ctggagatgg ttctgttaat gcat                                          24

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
gagggagcct cagaaacgg                                                19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
gtcgggagtg ggtaatttgc                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 25
tttttttttt tttttttttt                                                    20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 12-18 nucleotides
      according to the specification as filed

<400> SEQUENCE: 26
tttttttttt tttttttt                                                      18
```

COMPOSITIONS AND METHODS FOR CDNA SYNTHESIS

This application is a divisional of U.S. patent application Ser. No. 10/653,416 filed Sep. 3, 2003, which claims priority to U.S. Provisional Application No. 60/407,248 filed Sep. 3, 2002, the contents of which are incorporated herein by reference in its entirety.

FIELD OF THE INVENTION

The invention provides methods and compositions for preparing cDNA

BACKGROUND OF THE INVENTION

In examining the structure and physiology of an organism, tissue or cell, it often is desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is manifested only upon production of the protein encoded by the gene. To produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist many mRNA species, each encoding a separate and specific protein. This fact provides a powerful tool to investigators interested in studying genetic expression in a tissue or cell. mRNA molecules may be isolated and further manipulated by various molecular biological techniques, thereby allowing the elucidation of the full functional genetic content of a cell, tissue or organism. The identity and levels of specific mRNAs present in a particular sample provides clues to the biology of the particular tissue or sample being studied. Therefore, the detection, analysis, transcription, and amplification of RNAs are among the most important procedures in modern molecular biology.

A common approach to the study of gene expression is the production of complementary DNA (cDNA). In this technique, the mRNA molecules from an organism are isolated from an extract of the cells or tissues of the organism. From these purified mRNA molecules, cDNA copies may be made using the enzyme reverse transcriptase (RT) or DNA polymerases having RT activity, which results in the production of single-stranded cDNA molecules. The term "reverse transcriptase" describes a class of polymerases characterized as RNA dependent DNA polymerases. All known reverse transcriptases require a primer to synthesize a DNA transcript from an RNA template.

Avian myoblastosis virus (AMV) reverse transcriptase was the first widely used RNA dependent DNA polymerase (Verma, Biochem. Biophys. Acta 473:1(1977)). The enzyme has 5'-3' RNA directed DNA polymerase activity, 5'-3' DNA directed DNA polymerase activity, and RNase H activity. RNase H is a processive 5' and 3' ribonuclease specific for the RNA strand for RNA DNA hybrids (Perbal, A Practical Guide to Molecular Cloning, New York: Wiley & Sons (1984)). Errors in transcription cannot be corrected by reverse transcriptase because known viral reverse transcriptases lack the 3'-5' exonuclease activity necessary for proofreading (Saunders and Saunders, Microbial Genetics Applied to Biotechnology, London: Croom Helm (1987)). A detailed study of the activity of AMV reverse transcriptase and its associated RNase H activity has been presented by Berger et al., Biochemistry 22:2365 2372 (1983).

Another reverse transcriptase which is used extensively in molecular biology is reverse transcriptase originating from Moloney murine leukemia virus (M-MLV). See, e.g., Gerard, G. R., DNA 5:271 279 (1986) and Kotewicz, M. L., et al., Gene 35:249 258 (1985). M-MLV reverse transcriptase substantially lacking in RNase H activity has also been described. See, e.g., U.S. Pat. No. 5,244,797.

Historically, reverse transcriptase has been used primarily to transcribe mRNA into cDNA which can then be cloned into a vector for further manipulation. The single-stranded cDNAs may be converted into a complete double-stranded DNA copy (i.e., a double-stranded cDNA) of the original mRNA (and thus of the original double-stranded DNA sequence, encoding this mRNA, contained in the genome of the organism) by the action of a DNA polymerase. The double stranded cDNAs can then be inserted into a vector, transformed into an appropriate bacterial, yeast, animal or plant cell host, and propagated as a population of host cells containing a collection of cDNA clones, or cDNA library, that represents the genes, or portions of genes present in the original mRNA sample.

Alternatively, cDNA can be labeled with an appropriate reporter moiety and used as hybridization probe to query defined target sequences immobilized on glass slides, filters, or other suitable solid supports. The identity and relative abundance of a given mRNA in a sample can be inferred from the signal intensity for a specific target sequence on the solid support.

One of the most widely used techniques to study gene expression exploits first-strand cDNA for mRNA sequence(s) as template for amplification by the polymerase chain reaction, PCR. This method, often referred to as RNA PCR or reverse transcriptase PCR (RT-PCR), exploits the high sensitivity and specificity of the PCR process and is widely used for detection and quantification of RNA. Recently, the ability to measure the kinetics of a PCR reaction by on-line detection in combination with these RT-PCR techniques has enabled accurate and precise measurement of RNA sequences with high sensitivity. This has become possible by detecting the RT-PCR product through fluorescence monitoring and measurement of PCR product during the amplification process by fluorescent dual-labeled hybridization probe technologies, such as the "TaqMan" 5' fluorogenic nuclease assay described by Holland et al. (Proc. Natl. Acad. Sci. U.S.A. 88, 7276 (1991)), Gibson et al. (Genome Res. 6, 99 (1996)), and Heid et al. (Genome Res. 6, 986 (1996)); or "Molecular Beacons" (Tyagi, S. and Kramer, F. R. Nature Biotechnology 14, 303 (1996)). Nazarenko et al. (Nucleic. Acids Res. 25, 2516 (1997)) have described use of dual-labeled hairpin primers, as well as recent modifications utilizing primers labeled with only a single fluorophore (Nazerenko et al., Nucleic. Acids Res. (2002)). One of the more widely used methods is the addition of double-strand DNA-specific fluorescent dyes to the reaction such as: ethidium bromide (Higuchi et al., Biotechnology (1992) and Higuchi et al., Biotechnology 11, 102610, 413 (1993)), YO-PRO-1 (Ishiguro et al., Anal. Biochem. 229, 207 (1995)), or SYBR Green I (Wittwer et al., Biotechniques 22, 130 (1997)). These improvements in the PCR method have enabled simultaneous amplification and homogeneous detection of the amplified nucleic acid without purification of PCR product or separation by gel electrophoresis. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR, also referred to as quantitative PCR, or qPCR.

The general principals for template quantification by real-time PCR were first disclosed by Higuchi R, G Dollinger, P S Walsh and R. Griffith, "Simultaneous amplification and detection of specific DNA sequences", Bio/Technology 10:413-417, 1992; Higuchi R, C Fockler G Dollinger and R Watson, Kinetic PCR analysis: real time monitoring of DNA amplification reactions, Bio/Technology 11:1026-1030. This simpler approach for quantitative PCR utilizes a double-strand specific fluorescent dye, ethidium bromide, added to amplification reaction. The fluorescent signal generated at each cycle of PCR is proportional to the amount of PCR product. A plot of fluorescence versus cycle number is used to describe the kinetics of amplification and a fluorescence threshold level was used to define a fractional cycle number related to initial template concentration. Specifically, the log of the initial template concentration is inversely proportional to the fractional cycle number (threshold cycle, or Ct), defined as the intersection of the fluorescence versus cycle number curve with the fluorescence threshold. Higher amounts of starting template results in PCR detection at a lower Ct value, whereas lower amounts require a greater number of PCR cycles to achieve an equivalent fluorescent threshold (Ct) and are detected at higher Ct values. Typically, the setting of this fluorescence threshold is defined as a level that represents a statistically significant increase over background fluorescent noise. Since this occurs at an early stage in the PCR process when critical substrates are not limiting, quantification of starting template occurs over a broad dynamic range with high accuracy, precision, and sensitivity. A major problem in understanding of gene expression patterns for gene discovery and identification of metabolic pathways is the limitations of current methods for accurate quantification. Use of real time PCR methods provides a significant improvement towards this goal. However, real-time PCR quantification of mRNA is still bounded by limitations of the process of reverse transcription.

The RT-PCR procedure, carried out as either an end-point or real-time assay, involves two separate molecular syntheses: (i) the synthesis of cDNA from an RNA template; and (ii) the replication of the newly synthesized cDNA through PCR amplification. To attempt to address the technical problems often associated with RT-PCR, a number of protocols have been developed taking into account the three basic steps of the procedure: (a) the denaturation of RNA and the hybridization of reverse primer; (b) the synthesis of cDNA; and (c) PCR amplification. In the so called "uncoupled" RT-PCR procedure (e.g., two step RT-PCR), reverse transcription is performed as an independent step using the optimal buffer condition for reverse transcriptase activity. Following cDNA synthesis, the reaction is diluted to decrease $MgCl_2$, and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" RT PCR methods use a common or compromised buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{++}$ then PCR is carried out in the presence of $Mg^{++}$ after the removal of $Mn^{++}$ by a chelating agent. Finally, the "continuous" method (e.g., one step RT-PCR) integrates the three RT-PCR steps into a single continuous reaction that avoids the opening of the reaction tube for component or enzyme addition. Continuous RT-PCR has been described as a single enzyme system using the reverse transcriptase activity of thermostable Taq DNA Polymerase and Tth polymerase and as a two enzyme system using AMV RT and Taq DNA Polymerase wherein the initial 65° C. RNA denaturation step was omitted.

One step RT-PCR provides several advantages over uncoupled RT-PCR. One step RT-PCR requires less handling of the reaction mixture reagents and nucleic acid products than uncoupled RT-PCR (e.g., opening of the reaction tube for component or enzyme addition in between the two reaction steps), and is therefore less labor intensive, reducing the required number of person hours. One step RT-PCR also requires less sample, and reduces the risk of contamination (Sellner and Turbett, 1998). The sensitivity and specificity of one-step RT-PCR has proven well suited for studying expression levels of one to several genes in a given sample or the detection of pathogen RNA. Typically, this procedure has been limited to use of gene-specific primers to initiate cDNA synthesis.

In contrast, use of non-specific primer in the "uncoupled" RT-PCR procedure provides opportunity to capture all RNA sequences in a sample into first-strand cDNA, thus enabling the profiling and quantitative measurement of many different sequences in a sample, each by a separate PCR. The ability to increase the total amount of cDNA produced, and more particularly to produce cDNA that truly represents the mRNA population of the sample would provide a significant advance in study of gene expression. Specifically, such advances would greatly improve the probability of identifying genes which are responsible for disease in various tissues.

Ideally, synthesis of a cDNA molecule initiates at or near the 3'-termini of the mRNA molecules and terminates at the mRNA 5'-end, thereby generating "full-length" cDNA. Priming of cDNA synthesis at the 3'-termini at the poly A tail using an oligo dT primer ensures that the 3'-message of the mRNAs will be represented in the cDNA molecules produced. It would be very desirable if cDNA synthesis initiated at 3' end and continued to the 5'-end of mRNA's regardless of length of mRNA and the reverse transcriptase used. However, due to many factors such as length, nucleotide sequence composition, secondary structure of mRNA and also inadequate processivity of reverse transcriptases, cDNA synthesis prematurely terminates resulting in non-quantitative representation of different regions of mRNA (i.e. 3'-end sequences or 5'-end sequences). It has been demonstrated that use of mutant reverse transcriptases lacking RNase H activity result in longer cDNA synthesis and better representation, and higher sensitivity of detection. However, it is generally believed that using oligo dT primer results in cDNA sequence bias of mRNA 3'-end region.

In studies involving quantitative analysis of gene expression, sequence bias in the cDNA and non-quantitative representation of different parts of mRNA can yield inaccurate expression data. Due to these problems an alternative method of priming for cDNA synthesis has been used utilizing random primers. Due to random sequence, these primers are believed to non-specifically prime cDNA synthesis at arbitrary sites along the mRNA resulting shorter cDNA fragments that collectively represent all parts of mRNA in the cDNA population. Gerard and D'Alessio (1993 Methods in Molecular Biology 16:73-93) have reported that the ratio of random primer to mRNA is critical for efficient cDNA synthesis by M-MLV RT or its RNase H deficient derivatives.

Increasing concentrations of random hexamer resulted in increased yields of cDNA, however the average length of cDNA decreased accordingly. At equal hexamer concentrations, use of RNase H⁻ RT resulted in cDNA yields that were approximately 4 fold higher than that obtained with M-MLV RT. Ratios of hexamer to mRNA of 10:1 for M-MLV H-RT and 40:1 for M-MLV RT were reported to produce reasonable yields of cDNA without sacrificing length. This indicates that primer concentration must be optimized for different amounts of starting RNA template to achieve efficient cDNA synthesis efficiency. Since random primer has the potential to omit sequence close to the mRNA polyA tail, in some protocols, oligo dT primer and random primers have been used as mixtures and combine both priming methods.

The choice and concentration of primer can have a profound impact on the quantitative representation of different mRNA transcripts in first-strand cDNA. It is apparent therefore, that improved compositions and methods for improving the yield of cDNA produced using reverse transcription are greatly to be desired. It is also apparent that new methods for making collections or libraries of cDNA from cells or tissue that more accurately represent the relative amounts of mRNAs present in the cells or tissue are greatly to be desired. It is also apparent that more convenient compositions and kits for use in such methods are desirable.

SUMMARY OF THE INVENTION

The instant invention provides improved methods of synthesizing a cDNA molecule or molecules from an mRNA template or population of mRNA templates under conditions sufficient to increase the total amount of cDNA produced, and/or reduce RNA sequence bias in the resulting cDNA product. Specifically, the invention relates to the use of a mixture of oligo(dT) primer and random primer (e.g. hexameric, heptameric, octameric, nonameric, etc.) in a first-strand cDNA synthesis reaction. In accordance with the invention, any conditions that improve priming may be used. Such conditions preferably include, but are not limited to, optimizing primer concentrations, optimizing reaction temperatures and/or optimizing primer length or specificity. Such results may also be accomplished in accordance with the invention by optimizing the reverse transcription reaction, preferably by balancing the composition of salts or including enhancing agents that disrupt RNA secondary structure or improve the processivity of reverse transcriptase.

The present invention is also directed to compositions comprising mixtures of reagents, including reverse transcriptases, buffers, cofactors and other components, suitable for immediate use in conversion of RNA into cDNA and RT PCR without dilution or addition of further components. These compositions are useful, alone or in the form of kits, for cDNA synthesis or nucleic acid amplification (e.g., by the Polymerase Chain Reaction) or for any procedure utilizing reverse transcriptases in a variety of research, medical, diagnostic, forensic and agricultural applications.

It is therefore an object of this invention to provide new methods for reverse transcription of one or more nucleic acid molecules comprising incubating one or more nucleic acid templates in a buffer under conditions sufficient to make one or more first nucleic acid molecules complementary to all or a portion of the one or more templates, where the buffer comprises at least one reverse transcriptase, an effective amount of a mixture of random primers, where the random primers are present in a concentration of at least about 5 ng/µl, and an effective amount of oligo(dT), where the oligo(dT) is present in a concentration less than about 2 µM.

In accordance with further aspects of the invention the random primers may be present in a concentration of between about 5 ng/µl and about 20 ng/µl. The oligo(dT) may be present in a concentration of between about 25 nM and about 2 µM. The random primers may be between 5 and 10 nucleotides long, and may be are random hexamers. The oligo(dT) may consist essentially of between about 12 and about 25 dT residues, and may be an anchored oligo(dT) molecule containing a terminal non-T nucleotide or dinucleotide. The oligo (dT) may oligo(dT)$_{12-18}$ (SEQ ID NO: 26) or oligo(dT)$_{20}$ (SEQ ID NO: 25) or anchored equivalents thereof.

In another embodiment the reverse transcriptase may be a viral reverse transcriptase, and may be selected from the group consisting of AMV RT, RSV RT, MMLV RT, HIV RT, EIAV RT, RAV2 RT, TTH DNA polymerase, C.hydrogenoformans DNA polymerase, SUPERSCRIPT II RT, SUPERSCRIPT I RT, THERMOSCRIPT RT MMLV, ASLV and Rnase H⁻ mutants thereof. Mixtures of any of these reverse transcriptases may be used. In particular, mixtures of viral RT enzymes may be used, such as mixtures of MMLV and ASLV, and/or their RNAse H reduced or RNAse H⁻ analogs may be used.

It is another object of the invention to provide methods for reverse transcription of one or more nucleic acid molecules comprising incubating one or more nucleic acid templates in a buffer under conditions sufficient to make one or more first nucleic acid molecules complementary to all or a portion of the one or more templates, where the buffer comprises at least one reverse transcriptase, one or more primers suitable for priming reverse transcription of the one or more templates; and an effective amount of Li ion.

In accordance with further aspects of the invention the reverse transcriptase may be a viral reverse transcriptase, and may be selected from the group consisting of AMV RT, RSV RT, MMLV RT, HIV RT, EIAV RT, RAV2 RT, SUPERSCRIPT II RT, SUPERSCRIPT I RT, THERMOSCRIPT RT MMLV and Rnase H⁻ mutants thereof.

In one aspect of the invention, the Li ion may be present in a concentration of between about 5 mM to about 200 mM. The buffer may further comprise at least one additional monovalent cation in a concentration between about 20 mM and 200 mM, where the monovalent cation is selected from the group consisting of Na, K, and NH4, and where the total concentration of the Li ion and the further monovalent cation is less than or equal to about 200 mM. The additional monovalent cation may be K.

It is another object of the invention to provide a reagent mixture suitable for use in a reverse transcription reaction of at least one template nucleic acid, comprising glycerol in a concentration between about 10% and about 40%, a buffer and a reverse transcriptase, where the reagent mixture demonstrates prolonged stability when stored at −20° C. and may be used directly for a reverse transcription reaction without adding additional reverse transcriptase.

In one aspect of the invention, the buffer may comprise a monovalent cation selected from the group consisting of Li, Na, K and NH$_4$, a magnesium salt, a reducing agent, nucleoside triphosphates, and at least one non-ionic detergent. The buffer may further comprise at least one primer suitable for priming reverse transcription of a template by the reverse transcriptase. The mixture may also comprise an RNAse inhibitor protein. In one embodiment, the buffer comprises a potassium salt, a magnesium salt, nucleoside triphosphates, DTT, at least one primer suitable for priming reverse transcription of a template by the reverse transcriptase, at least one non-ionic detergent, and an RNAse inhibitor protein.

In any of these methods and compositions, two or more reverse transcriptases may be used, including any reverse transcriptase as described above. In any of these methods and compositions at least one thermostable DNA polymerase may also be present.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Table 1 shows sequences of qPCR Primers (SEQ ID NOS 1-24, respectively) and target mRNA Sequence Information. The specific primers and sequences are listed below:

```
CBP          CAGCGGCCAGACAGTTCCTG (SEQ ID NO:1);
196U20

CBP          TGCCCACCGTCGTTCTCGT (SEQ ID NO:2)
287L19

3'-APC       CCCAACTCCAGTGAATAACA (SEQ ID NO:3)
8433U20

3'-APC       AGAATGGCGCTTAGGACTT (SEQ ID NO:4)
8505L19

5'-APC       ACTGCGGTCAAAAATGTCCC (SEQ ID NO:5)
276U20

5'-APC       TCTCCAGAACGGCTTGATACAG (SEQ ID NO:6)
323122

RPA-32       GCAGGACCAGGGCGTTATAG (SEQ ID NO:7)
1248U20

RPA-32       CGTCATGGCAAGTGTGTCAAA (SEQ ID NO:8)
1380L23

3'-ADAR      CAGTCTTGGCACCCACAT (SEQ ID NO:9)
5702U18

3'-ADAR      AGCTCTGCTGGAGAACCTAA (SEQ ID NO:10)
5844L20

5'-ADAR      AATCCGCGGCAGGGGTATT (SEQ ID NO:11)
51U19

5'-ADAR      TGGGAGCTGCCCCTTGAGA (SEQ ID NO:12)
185L19

GAPDH        GAAGGTGAAGGTCGGAGTC (SEQ ID NO:13)
66U19

GAPDH        GAAGATGGTGATGGGATTTC (SEQ ID NO:14)
272L20 b-actin      GGCTACAGCTTCACCACCAC (SEQ ID NO:15)
630U20 b-actin      TGGCCATCTCTTGCTCGAAG (SEQ ID NO:16)
707L20

Kip1         CCGGTGGACCACGAAGAGT (SEQ ID NO:17)
103U19

Kip1         GCTCGCCTCTTCCATGTCTC (SEQ ID NO:18)
168L20

MAP4         CGGTCAGGCACACAAGGG (SEQ ID NO:19)
452U18

MAP4         GCATACACACAACAAAATGGCA (SEQ ID NO:20)
4569122

MAP4         CGGCGGCGGGCAGTT (SEQ ID NO:21)
63u15

MAP4         CTGGAGATGGTTCTGTTAATGCAT (SEQ ID NO:22)
113124

Hu 18s       GAGGGAGCCTCAGAAACGG (SEQ ID NO:23)
535U19

Hu 18s       GTCGGGAGTGGGTAATTTGC (SEQ ID NO:24)
602L20
```

Table 2 shows average $C_T$ values for SYBR Green qRT-PCR of first-strand cDNAs primed with varying amounts of random hexamer or oligo(dT)20 (SEQ ID NO: 25).

Table 3 shows average $C_T$ values for SYBR Green qRT-PCR of first-strand cDNAs synthesized in the presence of different cations. Bold text indicates lowest average $C_T$ for each reaction set. (NA=no amplification)

Table 4 shows stability information for various reaction mixtures for use in reverse transcription reactions. Table 4A shows the stability for RT Mix 1 after storage at −20° C. Table 4B shows the stability for RT Mix 2 at −20° C. Table 4C shows the stability for RT Mix 3 at −20° C.

DETAILED DESCRIPTION OF THE INVENTION

Surprisingly, it has been have found that by varying the concentration and ratios of oligo dT and random primers, efficiency of cDNA synthesis and uniform representation of mRNA sequences can be vastly improved. These improvements were realized using a fixed quantity of an oligo(dT) and random primer mixture over a wide range of starting RNA template amounts. Even though the ratio of primer to mRNA varied over 6 orders of magnitude, both the relative and absolute representation of mRNA sequence was maintained in the cDNA. In contrast to findings of earlier studies, it has been surprisingly discovered that even when using wild type reverse transcriptases with full RNase H activity, sensitivity of detection can be improved due to better and more efficient conversion of mRNA into cDNA.

An additional surprising discovery is that improved reaction conditions for cDNA synthesis can be obtained through the inclusion of an effective amount of a lithium salt in the reaction mixture, resulting in unexpectedly increased cDNA yield, particularly at low RNA template concentrations. Other embodiments of the invention relate to stabilized concentrated reaction mixtures for first-strand cDNA synthesis that simplify and improve the reliability of reverse transcription.

The present invention therefore relates to methods of increasing the efficiency of cDNA synthesis and more particularly, to increasing the sensitivity and accuracy of quantification of gene expression. Thus, the present invention provides improved cDNA synthesis useful in gene discovery, genomic research, diagnostics and identification of differentially expressed genes and identification of genes of importance to disease.

Use of Primer Combinations

Specifically, the present invention describes new primer combinations that provide more efficient and uniform priming for cDNA synthesis. The concentration and combinations of random primers and oligo dT used provides efficient and representative conversion of mRNA sequences into cDNA. This method provides superior and non-biased conversion of mRNA sequences into cDNA regardless of distance from 3' end of mRNA.

In one embodiment of this invention the random primers are mixed with oligo dT for priming cDNA synthesis. A variety of concentrations and ratios of each primer type can be used according to the method of the invention. Surprisingly it has been found that optimal amplification of some genes requires oligo dT while others require random primers. By combining both primer types as a mix this invention provides optimal cDNA synthesis and amplification for all mRNAs regardless of proximity of amplification region to 3' or 5' ends. The random primers used according to the invention can vary in size from 5 bases to 12 bases.

The length of oligo dT can vary from 8 bases to 30 bases. Other types of primers with different composition can be used in place of oligo dT. Examples of such compositions include, but are not limited to, oligo dT where the 3' base is A, or C, or G (anchored dT). Alternatively, two bases at the 3' end can be variable and can be any combination of A, C, or G. Other sequences or moieties that can base pair with poly A sequences of mRNA can also be used. An example, without limitation, is deoxy uridine, (dU).

The amount of random primers can vary from 25 ng to 800 ng for each reaction (20 uL), for example, 25, 50, 75, 100, 200, 300, 400, 500, 600, or 700 ng, or intermediate values. According to the methods of the invention the concentration of oligo dT can be 25 nM to 5000 nM, for example for example, 25, 50, 75, 100, 200, 300, 400, 500, 600, 700, 800, 900, 1000, 2000, 3000, or 4000 nM, or intermediate values. It will become evident to those skilled in the art that various ratios of random primers and oligo dT can be used.

The skilled artisan will recognize that when concentrations of random primers or oligo dT are specified as weight/volume ratios, the reagent concentrations obtained using such quantities will vary depending on the length of the primer and the attendant change in molecular weight. For example, the skilled worker will know that, when a method employs 12.5 ng/ml of random hexamers, an adjustment of quantity is required to achieve an equivalent concentration when random nonamers are used. Similar adjustments are made when using different lengths of oligo dT primers, such as oligo(dT)$_{20}$ (SEQ ID NO: 25) and oligo dT)$_{12-18}$ (SEQ ID NO: 26).

Use of Lithium Ion in RT and RT-PCR Reactions

In other embodiments of the present invention, it has been found that when lithium-containing compounds are included in the cDNA reaction the efficiency of cDNA synthesis is improved, resulting in higher sensitivity of detection and more accurate quantitation (see Examples). A variety of lithium containing salts and compounds can be used, and the skilled artisan will appreciate that the identity and concentration of the salt can be varied to optimize results. In the context of the present invention, an effective amount of a lithium salt is an amount sufficient to permit RT activity, or in the case of RT reactions that contain an additional monovalent cation such as K, that produce improved cDNA synthesis compared to the results produced in the absence of Li.

It is surprising that lithium can be used at all in RT reactions because it previously was thought that Li ion was inhibitory for a variety of retroviral enzymes and lithium is known to inhibit viral replication. The fact that lithium not only does not inhibit the reaction but produces improved results is particularly surprising.

Convenient and Stable Reagent Compositions

Another embodiment of the present invention is the form in which the reaction mixture is prepared and stably maintained. Traditionally, cDNA reaction components have been supplied as a number of separate components that are assembled into a complete reaction mix just prior to start of cDNA synthesis. Indeed, there is a widespread prejudice in the art that these components need to be kept separate for storage purposes. A typical kit for cDNA synthesis contains the following components:

a. Oligo(dT) 12-18 (SEQ ID NO: 26). 50 μl of a 0.5 mg/ml solution.
b. Random hexamers. 50 μl of a 50 ng/μl solution. This is a 25 μM solution.
c. 10× RT Buffer. 1 ml of solution containing 200 mM TrisCl pH 8.4, 500 mM KCl.
d. 25 mM MgCl2. 500 μl supplied.
e. 0.1 M DTT. 250 μl.
f. dNTP mix. 250 μl of a solution containing 10 mM each of dATP, dCTP, dGTP, dTTP.
g. SUPERSCRIPT II RT. 50 μl of enzyme at 50 U/μl.
h. *E. coli* RNase H. 50 μl of enzyme at 2 U/μl.
i. DEPC-treated water. 1.2 ml.
j. RNASEOUT™ Recombinant Ribonuclease Inhibitor. 100 μl supplied at 40 units/μl.

Each of the above components are provided separately and are frozen at −20° C. for storage. The above components are the components of SuperScript® 1$^{st}$ strand synthesis system for RT PCR from Invitrogen Corporation and is provided as a typical example of cDNA synthesis kits. All other commercially available kits are very similar. The general belief has been that the components can not be mixed for long term storage. A key component of these systems is reverse transcriptase that is always stored in special storage buffer with at least 50% glycerol, and is only added to the reaction mix immediately prior to start of cDNA synthesis.

Surprisingly, we have found that some or all of the components of the cDNA synthesis reaction can be combined and stored as a convenient ready-to-use mix that is stable to prolonged storage at −20° C. and that can simply be added to a nucleic acid template solution when needed. The ready to use reaction mixture may contain between about 10 and 40% glycerol, which is significantly less than the 50% or more that previously was thought necessary to maintain stability of the RT enzyme that is present in the mix.

The following is a formulation for a 5× cDNA mastermix that has successfully been produced and used for a variety of applications. The minimum components that may usefully be provided for the mixture are the glycerol, the RT and a suitable buffer component. Suitable buffer compounds, such as Tris-HCl, HEPES, etc, are well known in the art. Metal ions necessary for RT activity, such as Mg and a monovalent cation such as Li, K, Na, or NH$_4$ may be present in concentrations that are suitable for RT activity upon addition to a template solution. Additional components that may be present are a reducing agent, such as DTT, primer molecules such as gene specific primers, random primers of any suitable length, oligo (dT) compounds of any suitable length, anchored oligo(dT) molecules of suitable length, detergents or mixtures of detergents such as Tween, NP-40 and Igepal CA-630 and equivalent reagents, dNTPs, and one or more RNAse inhibitor proteins. The relative amounts contained in the mixture of such reagents necessary for use in RT reactions, when present, can be readily determined by the skilled artisan. In addition, at least one thermostable DNA polymerase may also be present, which may be used for subsequent PCR reactions or the like.

Accordingly, the present invention provides newly improved, convenient, and ready to use configurations for cDNA synthesis. The methods of the invention reduce the number additions for assembly of cDNA synthesis reactions which is highly sought by researchers especially in high throughput applications.

According to the methods of the invention, the ready to use mixes for cDNA synthesis can be made at different concentrations and provided as 1× to 20× "mastermixes." The following is an example of a 5× mastermix for cDNA synthesis that contains all components necessary for cDNA synthesis according to the methods of this invention. Using 4 uL of this mastermix and RNA preparation of interest at a total volume of 20 uL provides a complete reaction mix for conversion of RNA into cDNA. The skilled artisan will readily appreciate how to prepare suitable 1× to 20× mastermixes.

Formulation for 5× cDNA mastermind:
5× Buffer (0.1 M Tris-HCl, pH 8.4, 0.25M KCl)
0.1 M LiCl
25 mM MgCl2
2.5 mM dNTP (each)
50 mM DTT
500 nM oligo(dT)20(SEQ ID NO: 25)
50 ug/mL random primer
30 % Glycerol
0.005 % Igepal CA-630
0.005 % Tween 20
10,000 U/mL MMLV Rt
5000 U/mL Rnase inhibitor protein In addition to the above formulation, three other mastermixes were prepared that contained all reagents except the primers.

RT Mix 1 did not have primers
RT Mix 2 contained oligo dT as the primers
RT Mix 3 contained Random hexamers and Octamers as primers.

All of the above 5× cDNA mastermixes were found to be stable for months when stored at −20 C. Table 4 shows the results and the efficacy of cDNA synthesis with these mastermixes compared to the reagents stored separately under the conditions recommended in the literature.

It will be evident to those skilled in the art that a variety of different reverse transcriptases can be used according to the method of the invention. The reverse transcriptases may include, without limitation, AMV RT, RSV RT, MMLV RT, Rnase H− mutants of various reverse transcriptases, HIV RT, EIAV RT, RAV2 RT, TTH DNA polymerase, C.hydrogenoformans DNA polymerase, SUPERSCRIPT II RT, SUPERSCRIPT I RT, THERMOSCRIPT RT and mixtures thereof. It will also be obvious that one or more of the components of the above mastermix can be substituted with other equivalent reagent or protein. For example, there are a number of different RNAse inhibitor proteins that can be used. If desired, the RNAse inhibitor protein can also be excluded from the mixture since it is not always necessary for cDNA synthesis. Thermostable DNA polymerases suitable for use in the mastermixes are well known in the art and include Taq, Tth, Tne, Tma, Tli, Pfu, Pwo, Bst, Bca, Sac, Tac, Tfl/Tub, Tnt, Mth, Mtb, and Mlep DNA polymerases and the like.

The composition of the 5× buffer provided can also be varied, for example, by use of other buffers such as sulfate containing buffers or acetate based buffers that have been used for cDNA synthesis. It will be apparent to those skilled in the art that different formulations can be optimized for different applications.

As described supra, amplification of RNA sequences by PCR can be accomplished by a two step or a one step protocol. Mastermix formulations can be prepared for use in one step RT PCR by changing the primers and by inclusion of an appropriate thermostable DNA polymerase such as Taq DNA polymerase. A variety of formulations have been described for One-step RT PCR, however, in all cases the buffers and enzymes are kept separately and are only mixed immediately prior to reverse transcription reaction. According to the methods of the invention, the reverse transcriptase, Taq DNA polymerase and buffers, dNTP's, cofactors and all other components for one step RT PCR can be mixed together in a variety of different concentrations to provide a ready to use mastermix.

EXAMPLES

Methods:

RNA Isolation and Purification:

Total RNA from HeLa S3 cells was isolated using Trizol (Invitrogen, Carlsbad, Calif.) according to manufacturer's recommendation. Following treatment with RNase-free DNAse to degrade residual genomic DNA contamination, the RNA was purified by a silica spin cartridge, RNeasy, (Qiagen), and quantified by optical absorbance at 260 nm.

cDNA Synthesis:

First-strand cDNA synthesis was carried out using supplied components of the SUPERSCRIPT First-Strand Synthesis System for RT-PCR, (Invitrogen). In certain experiments, M-MLV RT, diluted to 50 U/μl in enzyme storage buffer, was substituted for SUPERSCRIPT II RT. Primers for cDNA synthesis, hexamer, octamer, or oligo(dT)$_{20}$ (SEQ ID NO: 25) were from Oligos Etc. Reactions (20 μl volumes) were assembled on ice with all required components including: buffer (20 mM Tris-HCl pH 8.4, 50 mM KCl); 0.5 mM each dNTP, 5 mM magnesium chloride, 10 mM dithiothreitol (DTT), 20 units Rnase inhibitor protein, 50 units of reverse transcriptase, varying amounts of HeLa cell total RNA, and primer(s) as indicated in each example. First-strand reactions were incubated 5-10 min at 25° C., followed by 30 minutes at 42° C. Following first-strand synthesis, reactions were heat-killed at 85° C. for 5 min., diluted in TE buffer and stored at 4° C.

Real-Time Quantitative PCR:

Real-time PCR was carried out in 50-μl reaction volumes using the iCycler and iQ SYBR Green Supermix (Bio-Rad Laboratories) according to manufacturer's recommendation. Target specific mastermixes were prepared with 300 nM each primer and dispensed as 40-μl volumes into 96-well PCR plates. cDNA sample (10 μl) was added to the appropriate wells and the plate was sealed with a clear heat-seal film (Marsh Bio Products). Reactions were mixed by vortexing then centrifuged briefly to collect contents in the bottom of each well. qPCRs were incubated for 3 min at 95° C. followed by 45 cycles of 95° C., 3 min.; 60 C, 30 s. Fluorescent signal was collected and analyzed at the 60° C. annealing/extension step.

Primer Sequences for qPCR:

Primers used for SYBR Green I real-time PCR were designed using the OLIGO software program (Molecular Biology Insights) or Primer Express (Applied Biosystems). Primer and target sequence information are summarized in the table 1.

The present invention, thus generally described, will be understood more readily by reference to the following examples, which are provided by way of illustration and are not intended to be limiting of the present invention.

Example I cDNA Priming Method Influences mRNA Quantification by Real-Time RT-PCR Varying amounts of random hexamer (25 ng, 50 ng, 100 ng, 200 ng, or 400 ng) or oligo(dT)$_{20}$ (SEQ ID NO: 25)(25 nM, 50 nM, 100 nM, 200 nM, 0.5 µM, 1 µM, or 2 µM) or a mixture of 250 ng hexamer and 100 nM oligo(dT)$_{20}$ (SEQ ID NO: 25) were used to prime first-strand cDNA synthesis from either 200 ng or 200 pg of HeLa cell total RNA in 20-µl volumes as describes above with either SUPERSCRIPT II or M-MLV RT. Each reaction was performed in triplicate. After completion of first-strand synthesis, reactions were diluted to 200 µl with 10 mM Tris-HCl, pH 8.4, 0.5 mM EDTA and 10-µl aliquots were used as template for SYBR Green real-time PCR with primer sets specific for a variety of human transcripts including: replication protein A (RPA), cyclin-dependent kinase inhibitor 1B (Kip1), nuclear cap binding protein (CBP), the 3'-end or 5'-end of RNA-specific adenosine deaminase (ADAR), the 3'-end or 5'-end of adenomatosis polyposis coli (APC), glyceraldehyde-3-phosphate dehydrogenase (GAPDH), β-actin, or r18s. Results for average cycle threshold ($C_T$) values obtained for each qPCR are summarized in Table 2.

Maximal sensitivity (lowest $C_T$) for each specific transcript varied with the choice and amount of cDNA primer. In general, higher concentrations of random hexamer resulted in increasing sensitivity of detection with optimal results obtained between 200 and 400 ng of hexamer primer. Results were consistent whether starting with 200 ng or 200 pg of total RNA template. These data contradict earlier studies that emphasized the importance of optimizing the ratio of random primer to RNA template. Furthermore, these results contradict those of Deprez et al., 2002. Anal Biochem. 307:63-69, who found random primer usage grossly inefficient for quantitative real-time PCR.

For some target sequences, use of oligo(dT)$_{20}$ (SEQ ID NO: 25) resulted in more sensitive detection than hexamer primer. RPA was detected approximately 2 $C_T$'s earlier (~4 fold) when cDNA was primed with oligo(dT)$_{20}$ (SEQ ID NO: 25) compared to hexamer. Surprisingly, sensitivity of detection for oligo(dT)-primed cDNA was relatively consistent from 50 nM to 2 µM for either SUPERSCRIPT II or M-MML RT. Most published cDNA protocols using oligo dT primer, or derivatives of oligo dT, use between 0.5 and 5 µM oligo dT. These data demonstrate that efficient cDNA synthesis can be obtained using much lower concentrations of primer. Surprisingly, the efficacy of oligo dT-primed cDNA with M-MLV was comparable to that obtained with SUPERSCRIPT II. Comparable qPCR results were obtained for 5'-regions of templates requiring reverse transcription of long mRNA sequences such as the ADAR or APC genes. Surprisingly, the efficacy of oligo dT-primed cDNA with M-MLV was comparable to that obtained with SUPERSCRIPT II. Comparable qPCR result were obtained for 5'-regions of templates requiring reverse transcription of long mRNA sequences such as the ADAR or APC genes.

For other target sequences (GAPDH, β-actin, 3'-end of ADAR) comparable sensitivities were obtained with either priming method.

Most significantly, use of a mixture of hexamer and oligo dT resulted in detection sensitivities for all target sequences that were comparable to those obtained using the favored cDNA priming method for any given target sequence. Therefore, use of a mixture of oligo dT and random primer is likely to result in more consistent performance and uniform cDNA synthesis efficiencies in studies involving genome-wide expression profiling.

Example II

Lithium Improves cDNA Yield and mRNA Quantification by Real-Time RT-PCR

First-stand cDNA syntheses were performed essentially as described above in 20 µL reaction volumes using 50 units of MMLV RT and 200 ng or 200 pg of HeLa total RNA. Reactions were primed using a mixture of 100 nM oligo(dT)20 (SEQ ID NO: 25), 125 ng random hexamer, and 12 ng random octamer. Control reactions contained a buffer of 20 mM Tris, pH 8.4, 50 mM KCl. Other reactions were supplemented with 20 mM LiCl, 20 mM KCl, 20 mM NaCl, or 20 mM ammonium sulfate. Each reaction was performed in duplicate. After completion of first-strand synthesis, reactions were diluted to 200 µl with 10 mM Tris-HCl, pH 8.4, 0.5 mM EDTA and 10-µl aliquots (1/20$^{th}$ of each cDNA reaction) were used as template for SYBR Green real-time PCR with primer sets specific for a variety of human transcripts including: replication protein A (RPA), cyclin-dependent kinase inhibitor 1B (Kip1), the 3'-end or 5'-end of RNA-specific adenosine deaminase (ADAR), the 3'-end or 5'-end of adenomatosis polyposis coli (APC), 3'-end or 5'-end of MAP4, β-actin, or r18s. Results for average cycle threshold ($C_T$) values obtained for each qPCR are summarized in Table 3.

In general, inclusion of lithium ion in the cDNA reaction resulted in detection of cDNA product at lower $C_T$s, indicating a higher cDNA synthesis efficiency and yield of cDNA product. Addition of 20 mM lithium, potassium, or sodium improved qRT-PCR from low input amounts of total RNA (200 pg) as compared to control reactions, with the exception of the 3'-end of MAP4. Addition of 20 mM ammonium ion either had little effect on $C_T$ or resulted in lower cDNA yield as reflected in delayed $C_T$s for RT-PCR product detection. On average, inclusion of lithium reduced Ct for detection of RT-PCR product from 10 pg of starting total RNA by 0.6 cycles compared to control reactions and 0.4 cycles compared to the addition of 20 mM potassium or sodium. Addition of lithium significantly improved the sensitivity of detection for the 3'-end of the APC transcript, as this RT-PCR product was not detected in control, or cDNA reactions supplemented with additional potassium or sodium. Similarly, the 5'-end of the ADAR transcript was not detected in control cDNA reaction. However, RT-PCR product was readily detected in lithium-containing cDNA reactions and was detected approximately 2 cycles earlier (~4 fold higher cDNA yield) as compared to cDNA reactions supplemented with an equivalent amount of potassium. Two-step qRT-PCR from higher amounts of total RNA template (200 ng) also showed improved detection sensitivities when lithium was included in the cDNA reaction. On the average, the $C_T$ for qRT-PCR product from lithium-containing cDNA reactions was 0.3 cycles lower than control reactions or reactions supplemented with 20 mM potassium, and 0.4 cycles lower than cDNA reactions containing 20 mM sodium. Collectively these data demonstrate that lithium ion improves the efficiency and yield of cDNA synthesis by retroviral reverse transcriptase.

Example III

Stability of cDNA Mastermixes

Three c DNA mastermixes were prepared according to the formulations described above and stored at −20 C. At the indicated times (table 4) the reagents were functionally tested by cDNA synthesis using 1 ug of Hela RNA as template. As control an identically prepared reagent set that had been stored separately (in buffers recommended in the literature) were also used to assemble a freshly made cDNA reaction. cDNA synthesis was for initiated at room temperature for 5 minutes followed by 30 min incubation at 42 C. The reactions were stopped by heat inactivation at 85 C for 5 min and were diluted 10 fold with TE buffer. The diluted samples were stored frozen until they were tested by Q-PCR using a set of primers for beta actin. Amplification protocol was as described in the amplification section above using the IQ SYBR green supermix and BioRad IQ cycler. Amplifications were performed in triplicates using $1/20^{th}$ of the cDNA reaction (50 ng of RNA analyzed in each amplification reaction).

What is claimed is:

1. A method for first strand cDNA synthesis comprising contacting one or more RNA molecules with a reagent mixture, wherein said reagent mixture comprises:
   (a) at least one reverse transcriptase;
   (b) a combination of primers wherein said combination comprises:
      (i) an effective amount of a mixture of random primers, wherein said random primers are present in a concentration of between about 5 ng/μl and about 20 ng/μl;
      (ii) an effective amount of oligo(dT), wherein said oligo (dT) is present in a concentration less than about 2 μM,
   and incubating the resulting solution under conditions suitable for first strand cDNA synthesis wherein said random primers and said oligo (dT) prime cDNA synthesis in a single step.

2. The method according to claim 1, wherein said oligo(dT) is present in a concentration of between about 25 nM and about 2 μM.

3. The method according to claim 1, wherein said random primers are between 5 and 10 nucleotides long.

4. The method according to claim 1, wherein said random primers are random hexamers.

5. The method according to claim 1, wherein said oligo(dT) consists essentially of between about 12 and about 25 dT residues.

6. The method according to claim 1, wherein said oligo(dT) is oligo(dT)$_{12-18}$(SEQ ID NO: 26) or oligo(dT)$_{20}$(SEQ ID NO: 25).

7. The method according to claim 1, wherein said at least one reverse transcriptase is a viral reverse transcriptase.

8. The method according to claim 1, wherein said reverse transcriptase is selected from the group consisting of AMV RT, RSV RT, MMLV RT, HIV RT, EIAV RT, RAV2 RT, TTH DNA polymerase, C.hydrogenoformans DNA polymerase, SUPERSCRIPT® I RT, SUPERSCRIPT® I RT, THERMOSCRIPT™ RT MMLV and Rnase H⁻ mutants thereof 9. The method of claim 1, further comprising: an effective amount of Li ion.

10. The method according to claim 9, wherein said reverse transcriptase is a viral reverse transcriptase.

11. The method according to claim 10, wherein said viral reverse transcriptase is selected from the group consisting of AMV RT, RSV RT, MMLV RT, HIV RT, EIAV RT, RAV2 RT, SUPERSCRIPT® II RT, SUPERSCRIPT® I RT, THERMOSCRIPT™ RT MMLV and Rnase H⁻ mutants thereof.

12. The method according to claim 9, wherein said Li ion is present in a concentration of between about 5 mM to about 200 mM.

13. The method according to claim 12, wherein said buffer further comprises at least one additional monovalent cation in a concentration between about 20 mM and 200 mM, wherein said monovalent cation is selected from the group consisting of Na, K, and NH4, and wherein the total concentration of said Li ion and said further monovalent cation is less than or equal to about 200 mM.

14. The method according to claim 13, wherein said additional monovalent cation is K.

15. The method according to claim 1, wherein said oligo (dT) is an anchored oligo(dT).

16. The method according to claim 15, wherein the 3' nucleotide of said anchored oligo(dT) is dA.

17. The method according to claim 15, wherein the 3' nucleotide of said anchored oligo(dT) is dC.

18. The method according to claim 15, wherein the 3' nucleotide of said anchored oligo(dT) is dG.

19. The method according to claim 15, wherein the 3' end of said anchored oligo(dT) is selected from the group consisting of dAdA, dAdG, dAdC, dGdG, dGdA, dGdC, dCdC, dCdA, and dCdG.

20. The method according to claim 1, wherein said oligo (dT) comprises at least one dU residue.

* * * * *